(12) United States Patent
Avicola et al.

(10) Patent No.: US 6,277,079 B1
(45) Date of Patent: Aug. 21, 2001

(54) FLASHING EARRING HEARTBEAT MONITOR

(76) Inventors: Ken Avicola, 4104 Whispering Oaks La., Danville, CA (US) 94506; Richard G. Morton, 17786 Aguamiel Rd., San Diego, CA (US) 92127; John R. Ross, P.O. Box 2138, Del Mar, CA (US) 92014

( * ) Notice: Subject to any disclaimer, the term of this patent is extended or adjusted under 35 U.S.C. 154(b) by 0 days.

(21) Appl. No.: 09/512,050

(22) Filed: Feb. 24, 2000

(51) Int. Cl.$^7$ .................................................... A61B 5/02
(52) U.S. Cl. .................. 600/502; 600/500; 362/104; 362/571; 362/800
(58) Field of Search .................. 362/104, 570–571, 362/800; 600/481, 500, 502, 310, 323

(56) References Cited

U.S. PATENT DOCUMENTS 4,296,459 * 10/1981 DeLuca ............................ 362/104 X
4,791,536 * 12/1988 James ............................... 362/104 X
4,912,608 * 3/1990 Lee .................................. 362/104 X

* cited by examiner

Primary Examiner—Angela D. Sykes
Assistant Examiner—Ryan Carter
(74) Attorney, Agent, or Firm—John R. Ross; John R. Ross, III

(57) ABSTRACT

An earring that flashes in synchronism with the wearer's heartbeat. A pulsed IR LED/photocell combination is built into an earring along with a comparator and a visible light-emitting source. The comparator determines when the heart has beat from the variation in the signal from the photocell and transmits a signal to a solid state switch to turn on the visible light-emitting source. Thus, the light emitting source flashes once for each heart beat. In a preferred use of the present invention a lover is able to determine when his or her partner is excited by observing the rate at which the partner's earring flashes. The invention may also be used for medical monitoring of patients.

11 Claims, 5 Drawing Sheets

FLASHING EARRING HEARTBEAT MONITOR

This application relates to earrings and heartbeat monitors.

BACKGROUND OF THE INVENTION

Flashing earrings are known. These are usually worn as novelty items. One such earring is an earring shaped like a small Christmas tree powered by a small battery. These earrings are seen occasionally at Christmas parties.

Many types of heartbeat monitors are known. These include pressure monitors; the simplest being a finger pressed against an artery. A well-known technique for measuring heartbeat utilizes a infrared (IR) light emitting diode (LED)/photocell combination. This technique is discussed in U.S. Pat. Nos. 4,239,048, 4,100,536 and 4,407,295, each of which are incorporated herein by reference. Infrared light will travel several centimeters through typical human skin tissue. Its absorption is much greater in blood. Thus, an IR LED is pressed against skin tissue near an artery and emits pulsed infrared light into the skin. A photocell is placed against the skin near the IR LED and measures light scattered from or transmitted through the skin. The signal received by the photocell varies as the blood surges in the tissue near the photocell and the IR LED with each beat of the person's heart. It is known that a person's earlobe is a good place to place the IR LED/photocell instrument since the carotid artery runs close to the ear. In prior art devices signals from the photocell are typically transmitted to a comparator, which calculates the rate of heart, beat and the resulting rate is displayed on a monitor.

What is needed is a simple method of displaying heartbeat by means of visible light flashes with a device that can be worn as a novelty item.

SUMMARY OF THE INVENTION

The present invention provides an earring that flashes in synchronism with the wearer's heartbeat. A pulsed IR LED/photocell combination is built into an earring along with a comparator and a visible light-emitting source. The comparator determines when the heart has beat from the variation in the signal from the photocell and transmits a signal to a solid state switch to turn on the visible light-emitting source. Thus, the light emitting source flashes once for each heart beat. In a preferred use of the present invention a lover is able to determine when his or her partner is excited by observing the rate at which the partner's earring flashes. The invention may also be used for medical monitoring of patients.

DETAILED DESCRIPTION OF PREFERRED EMBODIMENTS

First Preferred Embodiment

A first preferred embodiment of the present invention can be described by reference to the drawings.

IR Emitter, IR Detector and Visible Light Emitter

Figure 1A:
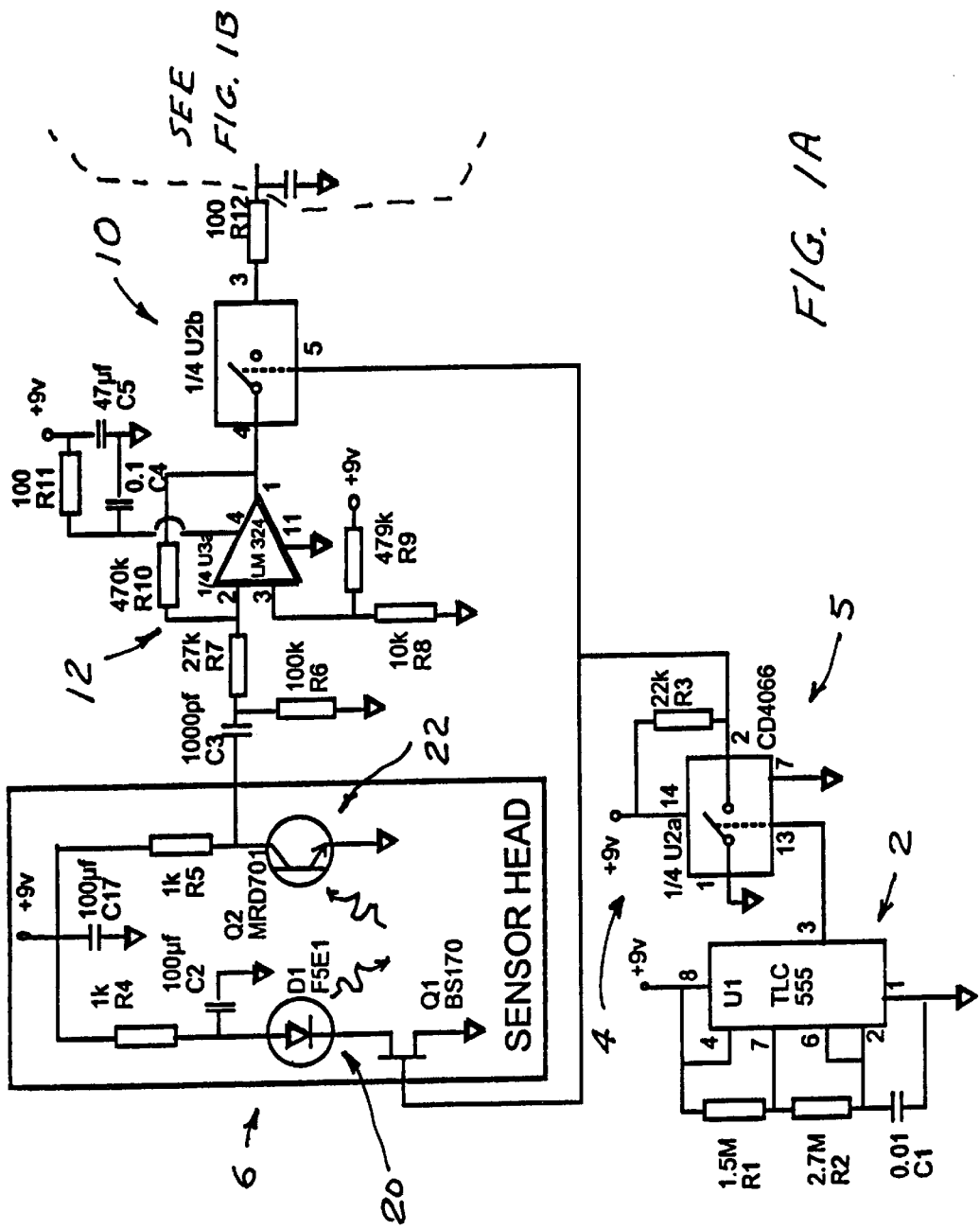
FIGS. 1A and 1B is a circuit diagram of a preferred of the present invention
Figure 1B:
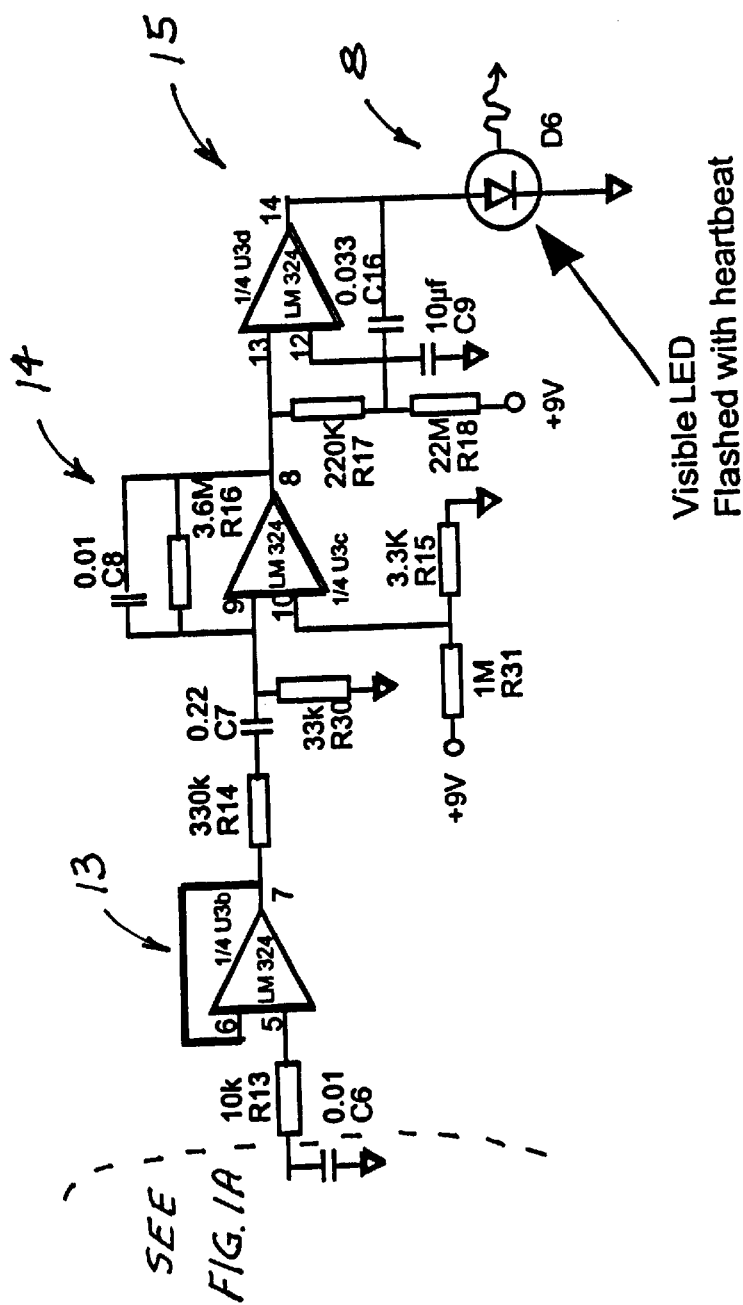
Figure 2:
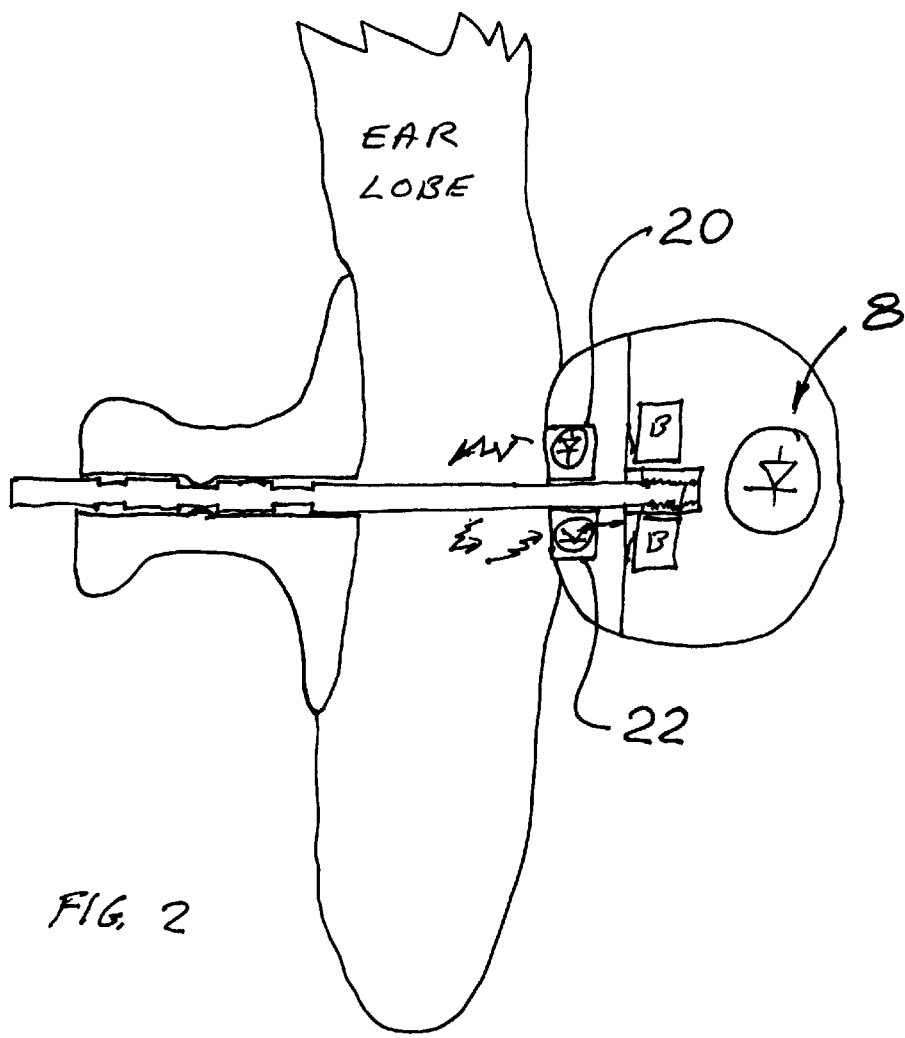
FIG. 2 is a drawing of a preferred embodiment mounted on a person's ear.
Figure 3:
FIG. 3 shows a person wearing a preferred embodiment.

FIGS. 1A and 1B is a circuit diagram of a preferred embodiment of the present invention. The sensor head of the embodiment is shown at 6. The sensor head includes an IR LED, D1F5E1 and a photocell Q2MRD701, which is a phototransistor. In this embodiment the photocell and the IR LED are located on the same side of the earlobe as shown in FIG. 2. In another embodiment the photocell and the IR LED will be located on opposite of the earlobe and the light from the IR LED passes through the lobe. In this embodiment as shown in FIG. 2, pulses of light from IR LED 20 are scattered in the earlobe and are detected by photocell 22. Electronics as described below and shown in FIGS. 1A and 1B detect the wearer's heartbeat and cause LED 8 to flash once for each beat of the heart. The earring shown in FIG. 2, except for the electronics, is of a standard design with rod 40 piercing the earlobe through an existing hole and a clip mechanism 42 on the neck side of the earlobe to hold the earring in place on the earlobe. Clip-type earrings could also be used for ears not pierced.

Electronics

The electronic and electro-optical components shown in FIGS. 1A and 1B are available from any of many commercial suppliers, such as Allied, Arrow and Avnet Electronics. The circuitry described in this embodiment provides all the functions needed to detect the heartbeat and drive LED 8 that emits visible red light.

Figure 4:
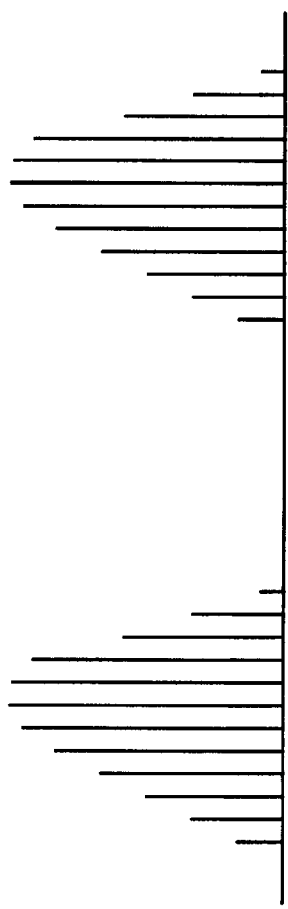
FIG. 4 shows a string of pulses moderated by blood pulsing in tissue.
Figure 5:
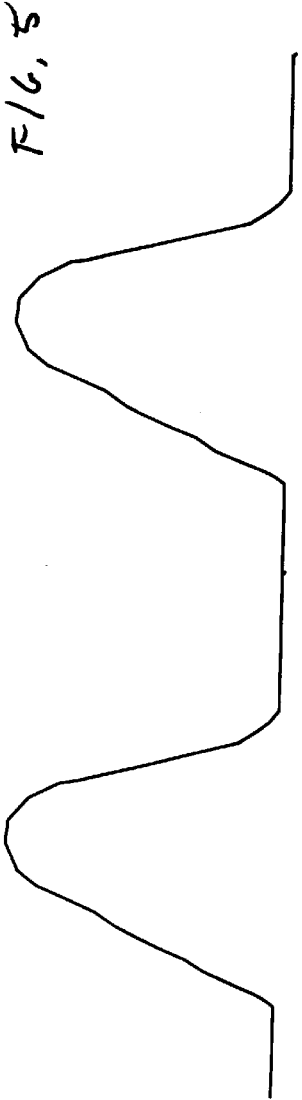
FIG. 5 shows a waveform used to trigger an LED.

U1 is an oscillator integrated circuit that is configured with R1 and R2 and with capacitor C1 to produces a 20-microsecond pulse at approximately 100 Hz. This signal is directed to pin 13 of U2a. U2a is ¼ of a quad bilateral switch that inverts the output of U1 to a positive going 20-microsecond pulse. This signal is directed to field effect transistor Q1 which in turn provides current to drive infrared light emitting diode (IR LED) D1 as shown as 20 in FIG. 1A. D1 produces a stream of IR pulses with a 20 micro second pulse width at a rate of about 100 pulses per second. Human hearts normally beat at rates between about 40 pulses per minute to about 200 pulses per minute; so this pulse frequency would provide about 30 to 150 pulses per heartbeat. These pulses of infrared light pass relatively well through the tissue of the earlobe but are preferentially absorbed in blood. Therefore, the amount of infrared light returning to the sensor head will vary depending on how much blood the light encounters in the earlobe. Since the amount of blood in the earlobe varies significantly during each heartbeat the returning light will also vary significantly. Phototransistor Q2 shown as 22 in FIG. 1A is mounted next to D1 and D1 and Q2 form the heartbeat sensor head. U3 is an integrated circuit with four Op Amps. Op Amp U3a amplifies the pulse stream out of phototransistor Q2. Integrator circuit 10 comprising IC switch U2b in conjunction with R12 and C6 recovers the heartbeat pulse envelope from the modulated pulse stream out of U3a. A typical waveform out of U3a is shown in FIG. 4. This waveform (portraying about 50 pulses per heartbeat) would correspond to a heart beating at a rate of about 120 beats per minute (two beats per second) which would correspond to a jogging heart rate of a person in good physical shape or to a very excited lover. Switch U2b is controlled by the same oscillator used to generate the IR pulses and is thus synchronized with these pulses. The switch closes during each 20-microsecond pulse charging integrating capacitor C6 to the peak of the pulse. The process is repeated with each successive pulse with the result that capacitor C6 reconstructs the heartbeat waveform from the pulse stream shown in FIG. 4. Amplifier circuit 13 comprises Op Amp U3b (LM324) acts as a high impedance buffer between the integrator circuit and the next amplifier circuit 14. Amplifier circuit 14 comprises amplifier U3c (LM324) which provides further amplification and filtering of the recovered waveform. An example of this recovered waveform is illustrated in FIG. 5. Filter network R14, R30 and C7 form a hi-pass filter and filter network R16 and C8 form a low-pass filter. The passband is from 2.2 Hz to 4.4 Hz. These filters together pass the recovered heartbeat waveform, while rejecting all other frequencies outside the desired passband. This filtering technique improves the signal-to-noise ratio of the circuit and enhances the ability of this preferred embodiment to detect the heartbeat without false triggers.

The reproduced heartbeat at the output of U3c (pin 8) is positive going with amplitude of approximately 0.3 volts. Op-Amp U3d is configured as a comparator and is biased by the resistor network R17 and R18 so that the positive comparator input (pin 12) is at about +0.1 volt. The heartbeat signal is applied to the negative comparator output (pin 14) is driven from +9 volts to 1 volts. When the output is driven to zero volts, the +9 volt supply provides the drive current to the LED through the limiting resistor R28. This provides the drive current to "turn on" the LED (D6). LED D6 remains "on" until the waveform at pin 13 drops below the reference voltage on pin 12. Thus we get a flash of visible light from LED D6 shown at 8 in FIG. 1B and in FIG. 2 for each detected heartbeat.

Second Preferred Embodiment

Figure 6:
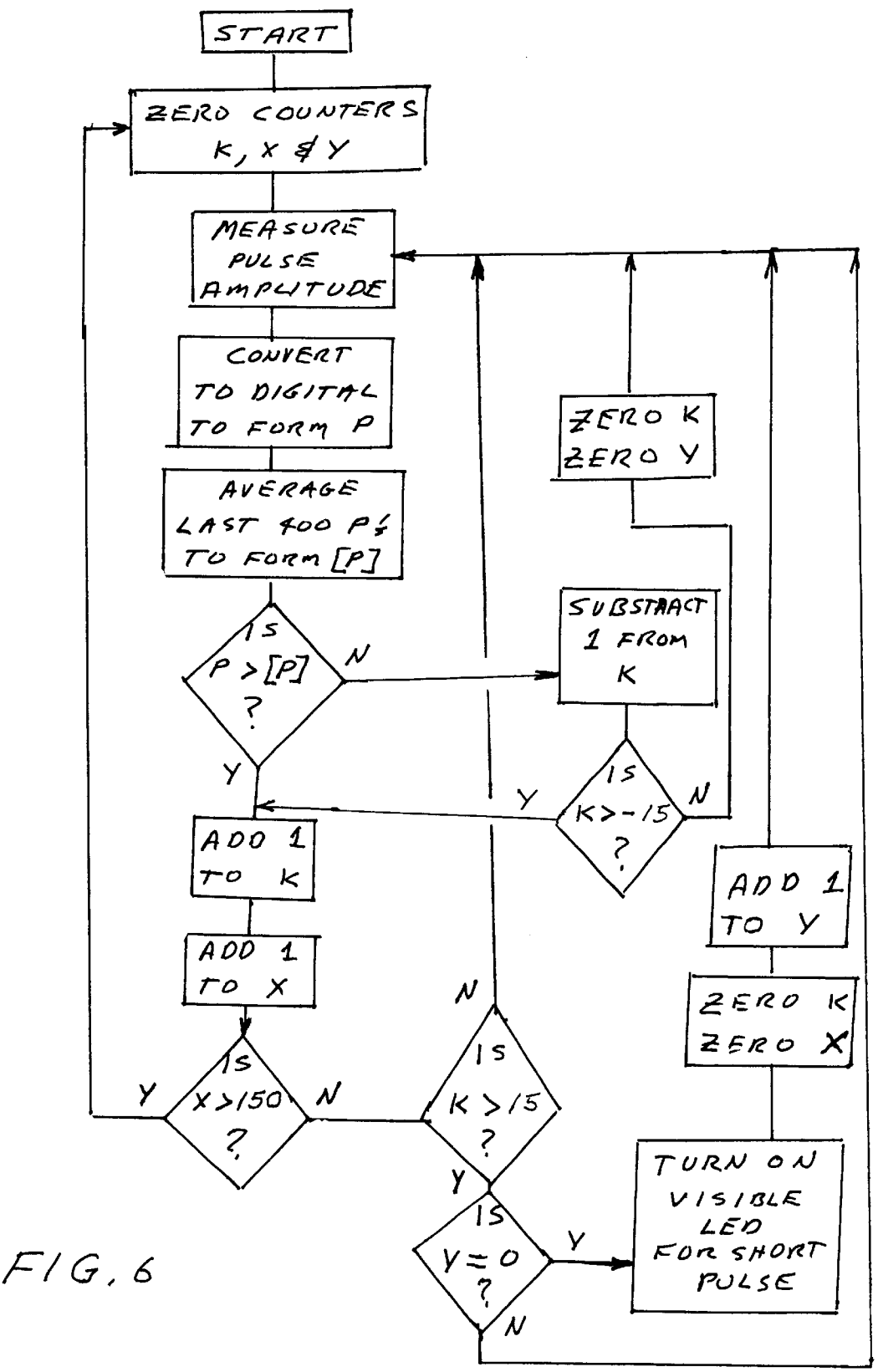
FIG. 6 is a flow chart of the software of a preferred embodiment.

In a second preferred embodiment the pulses from IR detector 22 are digitized by a very small microprocessor that is also used to analyze the digitized pulses and to turn on visible light source 8 for a short pulse for each heartbeat. FIG. 6 is a flow diagram showing a preferred technique for programming the microprocessor. The program converts the amplitude of each pulse into a digital value P. It calculates an average pulse amplitude [P] against which P is compared. The program turns on the visible light source 8 when the number of pulses having amplitudes in excess of the average amplitude is greater than 15 more than the number of pulses having amplitudes less than or equal to the average amplitude. After a pulse the earring will not pulse again until the number of pulses with below average amplitude is more than 15 greater than the number of pulses with amplitudes greater than the average amplitude. The P in FIG. 4 shows when the visible light pulse would be triggered in the example shown. If heartbeats are not being detected but the 100 Hz pulses are being detected with random amplitudes, statistical variations will soon produce a pulse. To reduce these false pulses, the counters are re-zeroed after a number of pulses. In this embodiment that number is 150 pulses which is the number of pulses per heartbeat at 40 beats per minute. In a more sophisticated embodiment the re-zero number could be calculated based on the measured pulse rate; so that a smaller re-zero number would be used when the wearer's heartbeat rate is greater than 40 beats per minute.

Other Embodiments

The embodiment of the present invention described above can be produced from components readily available from electronics parts suppliers such as the ones listed above. The earrings made from these parts including a hearing aid battery can be made small enough to fit into an earring as small as about 3 to 4 cm$^3$. Utilizing application specific integrated circuit (ASIC) concepts, the earrings (including the battery) can be packaged into an earring as small as 1 cm$^3$ or smaller.

Preferably the battery for the unit will be a rechargeable battery and the earrings can be marketed with a case, which includes a charging circuit powered by standard 120 volt AC so that when the earrings are not in use, the earring batteries can be easily recharged.

Although the present invention has been described in terms of specific embodiments, it is understood that many other embodiments of the present invention are possible. For example, the pulse rate of the oscillator could be larger or smaller than 100 Hz; however at least 10 Hz is recommended. A photodiode could be used instead of the specified phototransistor. Many circuits other than the one described in detail above could be used to determine the heart beat from the detected modulating IR pulses. For example, a continuous IR source and corresponding detection circuitry could be implemented. For these reasons the scope of the present invention should be determined by the appended claims and their legal equivalents.

We claim:

1. A flashing earring comprising:
   A) an attachment mechanism for attaching said earring to an earlobe of a wearer,
   B) an infrared emitter positioned to emit infrared light into the tissue of the earlobe,
   C) a first power source for causing said infrared emitter to emit infrared,
   D) an infrared photo-detector positioned so as to detect infrared light emanating from the earlobe and to produce electrical signals corresponding to the detected infrared light,
   E) an analyzing circuit for analyzing the electrical signals from said photo-detector to detect each beat of the wearer's heart,
   F) a visible light emitter,
   G) a trigger circuit for initiating electrical pulses to cause said visible light emitter to flash once for each beat signal;
   wherein said visible light emitter emits a flash of visible light each time the wearer's heart beats.

2. A flashing earring as in claim 1 wherein said first power source is a pulse power source for producing electrical pulses at rates of at least 10 Hz to cause said infrared emitter to emit IR pulses at rates of at least 10 Hz.

3. A flashing earring as in claim 1 wherein said analyzing circuit comprises integrated circuits for converting electrical signals from said photo-detector into waveforms corresponding to said heart beats.

4. A flashing earring as in claim 2 wherein said analyzing circuit comprises integrated circuits for comparing said waveforms to a reference signal so as to initiate said electrical pulses to produce said flashes.

5. A flashing earring as in claim 1 wherein said analyzing circuit comprises an analog-to-digital converter to produce digital signals corresponding to said detected pulses and a microprocessor to analyze said digital signals.

6. A flashing earring as in claim 4 wherein said processor is programmed with software which calculates average values of pulse amplitude and counts pulses having amplitudes in excess of said average values to determine when the wearer's heart has beat.

7. A flashing earring as in claim 5 wherein said software also directs said trigger circuit to initiate said flash.

8. A flashing earring as in claim 1 wherein said infrared emitter is an IR LED.

9. A flashing earring as in claim 1 wherein said photo-detector is a photocell.

10. A flashing earring as in claim 8 wherein said photocell is a phototransistor.

11. A flashing earring as in claim 8 wherein said photocell is a photodiode.

* * * * *